United States Patent
Yamaguchi

(10) Patent No.: US 9,305,755 B2
(45) Date of Patent: Apr. 5, 2016

(54) MASS ANALYSIS DATA PROCESSING METHOD AND MASS ANALYSIS DATA PROCESSING APPARATUS

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1050 days.

(21) Appl. No.: 13/263,066

(22) PCT Filed: Apr. 7, 2009

(86) PCT No.: PCT/JP2009/001614
§ 371 (c)(1),
(2), (4) Date: Nov. 14, 2011

(87) PCT Pub. No.: WO2010/116409
PCT Pub. Date: Oct. 14, 2010

(65) Prior Publication Data
US 2012/0191369 A1 Jul. 26, 2012

(51) Int. Cl.
*H01J 49/26* (2006.01)
*G01D 7/02* (2006.01)
(Continued)

(52) U.S. Cl.
CPC ............ *H01J 49/0036* (2013.01); *G01D 7/02* (2013.01); *G06F 19/703* (2013.01); *H01J 49/26* (2013.01); *G06F 17/40* (2013.01); *G06F 19/00* (2013.01)

(58) Field of Classification Search
CPC ............ G01D 7/00; G01D 7/02; G01D 7/04; G01D 7/06; G01D 7/08; G01D 9/00; G01D 21/00; G01N 27/00; G01N 27/62; G01N 27/622; G01N 30/00; G01N 30/02; G01N 30/86; G01N 30/8624; G01N 30/8631; G01N 2030/86; G01N 2030/48; G01N 30/8651; G01N 30/8655; G01N 30/88; G06F 11/00; G06F 11/30; G06F 11/32; G06F 11/34; G06F 15/00; G06F 15/16; G06F 17/00; G06F 17/10; G06F 17/40; G06F 19/00; H01J 49/00; H01J 49/0027; H01J 49/0036; H01J 49/004; H01J 49/26
USPC ............ 73/19.01, 19.02, 19.12, 23.3, 23.35, 73/23.36, 23.37, 53.01, 64.54, 432.1, 73/865.8, 865.9, 866.3; 250/281, 282; 340/500, 540; 702/1, 22, 23, 24, 25, 702/26, 30, 31, 127, 128, 187, 189; 708/100, 105, 200; 715/200, 273, 277
See application file for complete search history.

(56) References Cited

U.S. PATENT DOCUMENTS 7,645,984 B2 * 1/2010 Gorenstein et al. ............ 250/281
8,017,908 B2 * 9/2011 Gorenstein et al. ............ 250/282
(Continued)

FOREIGN PATENT DOCUMENTS

EP 1507237 A2 2/2005
EP 1727066 A2 11/2006
(Continued)

OTHER PUBLICATIONS

Applied Biosystems, Internet "MarkerView Software", [online] URL, appliedbiosystems.co.jp/website/jp/product/modelpage.jsp?MODELCD=97189 Mar. 11, 2009.
(Continued)

*Primary Examiner* — Edward Cosimano
(74) *Attorney, Agent, or Firm* — Morgan, Lewis & Bockius LLP

(57) ABSTRACT

From the data obtained by an LC/MS analysis in which an automatic $MS^n$ analysis is performed, all $MS^2$ spectrum data are collected (S1), and a data matrix is created whose elements are peak intensity data with different precursor ions being arrayed in the horizontal direction and the mass-to-charge ratio of the product ions in the vertical direction (S2). By using the data in this data matrix, the correlation coefficients between two precursor ions are computed to create a correlation coefficient matrix (S3). In the correlation coefficient matrix, the diagonal elements whose value is "1" are all replaced by "0" to create an adjacency matrix (S4). A network analysis is performed for the adjacency matrix to create a network map showing the correlations among different precursor ions ($MS^2$ spectra) (S5). The network map is displayed on a window of a display unit simultaneously with the result of an $MS^1$ analysis to provide an analysis operator with information on the compounds contained in a sample or the structure thereof (S6).

19 Claims, 7 Drawing Sheets

(51) Int. Cl.
*G06F 17/40* (2006.01)
*G06F 19/00* (2011.01)
*H01J 49/00* (2006.01)

(56) References Cited

U.S. PATENT DOCUMENTS

| | | |
|---|---|---|
| 2005/0039123 A1 | 2/2005 | Kuchinsky et al. |
| 2005/0278321 A1 | 12/2005 | Vailaya et al. |
| 2007/0059842 A1 | 3/2007 | Yamashita et al. |
| 2007/0174019 A1 | 7/2007 | Vailaya et al. |
| 2007/0278395 A1* | 12/2007 | Gorenstein et al. ........... 250/282 |
| 2008/0073501 A1 | 3/2008 | Yamaguchi et al. |
| 2009/0008548 A1 | 1/2009 | Yamaguchi |
| 2010/0187414 A1* | 7/2010 | Gorenstein et al. ........... 250/282 |
| 2013/0096847 A1* | 4/2013 | Yamaguchi ..................... 702/23 |
| 2014/0156203 A1* | 6/2014 | Yamaguchi ..................... 702/23 |

FOREIGN PATENT DOCUMENTS

| | | |
|---|---|---|
| EP | 1736902 A1 | 12/2006 |
| JP | 10-293120 A | 11/1998 |
| JP | 2006323846 A | 11/2006 |
| JP | 2007004807 A | 1/2007 |
| JP | 2007285719 A | 11/2007 |
| JP | 4058449 B2 | 3/2008 |
| JP | 2009014424 A | 1/2009 |
| JP | 2009025056 A | 2/2009 |
| JP | 2009-053070 A * | 3/2009 |
| WO | 2004113905 A1 | 12/2004 |

OTHER PUBLICATIONS

Jun Yonekubo et al., "Feature of newest Time of Flight Mass Spectrometer LCT Premier and Applied for Food Metabolome" (with English abstract) Chromatography, vol. 27, No. 2, pp. 85-89, 2006.

Tetsuo Iida et al., "Application of LCMS-IT-TOF Mass Spectrometer for Proteomics Analysis" (with English abstract) Shimadzu Review, vol. 63, Nos. 1-2, pp. 19-28, Sep. 29, 2006.

Japanese language international preliminary report on patentability dated Nov. 15, 2011 and its English language translation for corresponding PCT application PCT/JP2009/001614.

Japanese language office action dated Feb. 5, 2013 and its English language translation issued in corresponding Japanese application 2011508066.

Examination Report Received for Japanese Patent Application No. 2013-080185, mailed on Dec. 24, 2014, 4 pages (2 pages of English Translation and 2 pages of Official Copy).

* cited by examiner

TOTAL ION CHROMATOGRAM

MS$^1$ SPECTRA

MS$^2$ SPECTRA

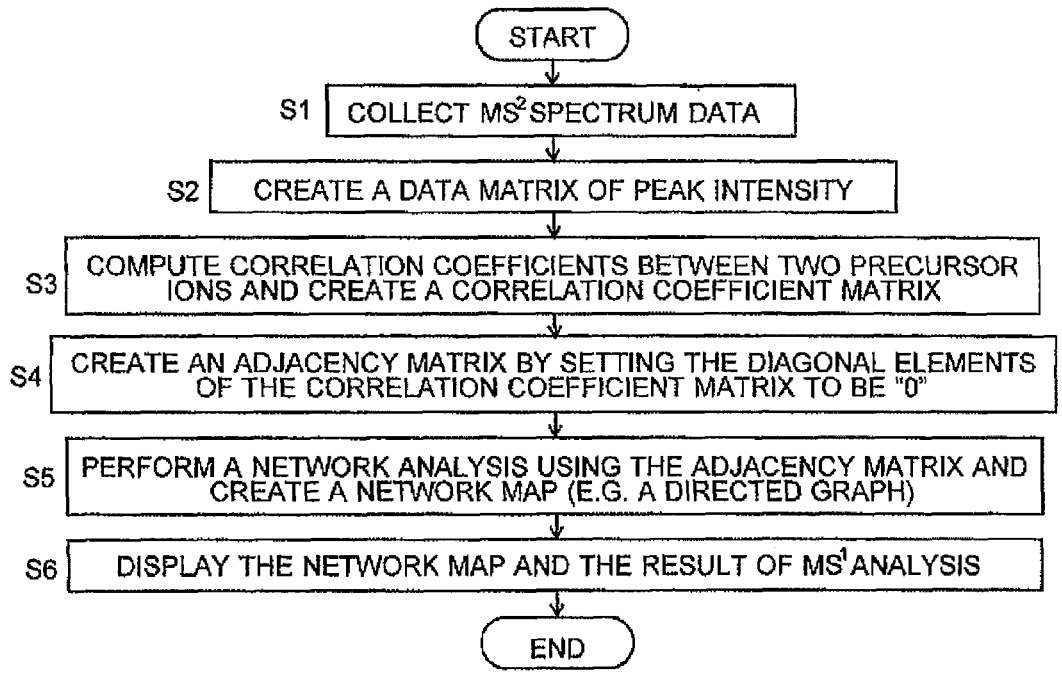
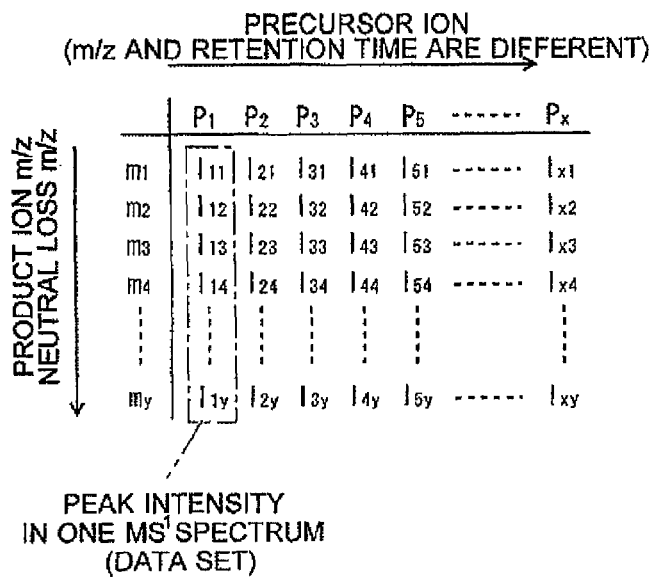

Fig. 5

PRECURSOR ION
(m/z AND RETENTION TIME ARE DIFFERENT) →

|   | $P_1$ | $P_2$ | $P_3$ | $P_4$ | $P_5$ | ------ | $P_x$ |
|---|---|---|---|---|---|---|---|
| $P_1$ | 1 | $R_{12}$ | $R_{13}$ | $R_{14}$ | $R_{15}$ | ------ | $R_{1x}$ |
| $P_2$ | $R_{12}$ | 1 | $R_{23}$ | $R_{24}$ | $R_{25}$ | ------ | $R_{2x}$ |
| $P_3$ | $R_{13}$ | $R_{23}$ | 1 | $R_{34}$ | $R_{35}$ | ------ | $R_{3x}$ |
| $P_4$ | $R_{14}$ | $R_{24}$ | $R_{34}$ | 1 | $R_{45}$ | ------ | $R_{4x}$ |
| ⋮ | ⋮ | ⋮ | ⋮ | ⋮ | | | ⋮ |
| $P_x$ | $R_{1x}$ | $R_{2x}$ | $R_{3x}$ | $R_{4x}$ | $R_{5x}$ | ------ | 1 |

(PRECURSOR ION, vertical axis ↓)

Fig. 6

|   | $P_1$ | $P_2$ | $P_3$ | $P_4$ | $P_5$ | ------ | $P_x$ |
|---|---|---|---|---|---|---|---|
| $P_1$ | 0 | $R_{12}$ | $R_{13}$ | $R_{14}$ | $R_{15}$ | ------ | $R_{1x}$ |
| $P_2$ | $R_{12}$ | 0 | $R_{23}$ | $R_{24}$ | $R_{25}$ | ------ | $R_{2x}$ |
| $P_3$ | $R_{13}$ | $R_{23}$ | 0 | $R_{34}$ | $R_{35}$ | ------ | $R_{3x}$ |
| $P_4$ | $R_{14}$ | $R_{24}$ | $R_{34}$ | 0 | $R_{45}$ | ------ | $R_{4x}$ |
| ⋮ | ⋮ | ⋮ | ⋮ | ⋮ | | | ⋮ |
| $P_x$ | $R_{1x}$ | $R_{2x}$ | $R_{3x}$ | $R_{4x}$ | $R_{5x}$ | ------ | 0 |

Fig. 7

[$MS^2$ DATA MATRIX]

|   |   | $P_1$ | $P_2$ | $P_3$ | $P_4$ | $P_5$ |
|---|---|---|---|---|---|---|
|   | RT | 14.243333 | 0 | 0.15 | 0.15 | 0.3 |
|   | M(m/z) | 455.2913 | 279.1628 | 297.082 | 281.0515 | 223.0708 |
|   | m/z | | | | | |
| $m_1$ | 100.049 | 0 | 0 | 0 | 0 | 0 |
| $m_2$ | 100.0833 | 0 | 0 | 0 | 0 | 0 |
| $m_3$ | 100.1062 | 0 | 0 | 0 | 0 | 0 |
| $m_4$ | 100.3809 | 0 | 0 | 0 | 0 | 0 |
| $m_5$ | 102.7354 | 0 | 0 | 0 | 0 | 0 |
| $m_6$ | 103.7293 | 0.0574 | 0 | 0 | 0 | 0 |
| $m_7$ | 104.6212 | 0 | 0 | 0 | 0 | 0 |
| $m_8$ | 104.6393 | 0 | 0 | 0 | 0 | 0 |
| $m_9$ | 105.2834 | 0 | 0 | 0 | 0 | 0 |
| $m_{10}$ | 106.5885 | 0 | 0 | 0 | 0 | 0 |
| $m_{11}$ | 106.0471 | 0 | 0 | 0 | 0 | 0 |
| $m_{12}$ | 106.05595 | 0 | 0 | 0 | 0 | 0 |
| $m_{13}$ | 106.0622 | 0 | 0 | 0 | 0 | 0 |
| $m_{14}$ | 106.0751 | 0 | 0 | 0 | 1.9481 | 0 |

Fig. 8

[CORRELATION COEFFICIENT MATRIX]

|    | P₁ | P₂ | P₃ | P₄ | P₅ | P₆ | P₇ | P₈ |
|----|----|----|----|----|----|----|----|----|
| P₁ | 1 | −0.0025 | −0.00521 | −00444 | −0.0025 | −0.00396 | −0.00463 | −0.0025 |
| P₂ | −0.0025 | 1 | −0.00244 | −0.00208 | −0.00118 | 0.313476 | −0.00217 | −0.00118 |
| P₃ | −0.00521 | −0.00244 | 1 | −0.00398 | 0.187796 | −0.00386 | 0.318429 | −0.00244 |
| P₄ | −0.00444 | −0.00208 | −0.00398 | 1 | −0.00208 | −0.00329 | 0.197308 | −0.00208 |
| P₅ | −0.0025 | −0.00118 | 0.187796 | −0.00208 | 1 | −0.00186 | −0.00217 | −0.00118 |
| P₆ | −0.00396 | 0.313476 | −0.00386 | −0.00329 | −0.00186 | 1 | −0.00118 | −0.00186 |
| P₇ | −0.00463 | −0.00217 | 0.318429 | 0.197308 | −0.00217 | −0.00118 | 1 | −0.00217 |
| P₈ | −0.0025 | −0.00118 | −0.00244 | −0.00208 | −0.00118 | −0.00186 | −0.00217 | 1 |

Fig. 9

[ADJACENCY MATRIX]

|    | P₁ | P₂ | P₃ | P₄ | P₅ | P₆ | P₇ | P₈ |
|----|----|----|----|----|----|----|----|----|
| P₁ | 0 | −0.0025 | −0.00521 | −00444 | −0.0025 | −0.00396 | −0.00463 | −0.0025 |
| P₂ | −0.0025 | 0 | −0.00244 | −0.00208 | −0.00118 | 0.313476 | −0.00217 | −0.00118 |
| P₃ | −0.00521 | −0.00244 | 0 | −0.00398 | 0.187796 | −0.00386 | 0.318429 | −0.00244 |
| P₄ | −0.00444 | −0.00208 | −0.00398 | 0 | −0.00208 | −0.00329 | 0.197308 | −0.00208 |
| P₅ | −0.0025 | −0.00118 | 0.187796 | −0.00208 | 0 | −0.00186 | −0.00217 | −0.00118 |
| P₆ | −0.00396 | 0.313476 | −0.00386 | −0.00329 | −0.00186 | 0 | −0.00118 | −0.00186 |
| P₇ | −0.00463 | −0.00217 | 0.318429 | 0.197308 | −0.00217 | −0.00118 | 0 | −0.00217 |
| P₈ | −0.0025 | −0.00118 | −0.00244 | −0.00208 | −0.00118 | −0.00186 | −0.00217 | 0 |

DISPLAY EXAMPLE OF OVERLAPPING THE MS1 ANALYSIS RESULT AND MS/MS ANALYSIS RESULT
MS1 ANALYSIS RESULT   MS/MS ANALYSIS RESULTS (CLUSTER)

DISPLAY EXAMPLE OF THE RESULT OF AN MS/MS MULTIVARIATE ANALYSIS
(CLUSTERS BY A NETWORK ANALYSIS)

MASS ANALYSIS DATA PROCESSING METHOD AND MASS ANALYSIS DATA PROCESSING APPARATUS

CROSS-REFERENCE TO THE RELATED APPLICATIONS

The present application is a national stage of international application No. PCT/JP2009/001614, filed on Apr. 7, 2009, the entire contents of which are incorporated herein by reference.

TECHNICAL FIELD

The present invention relates to a data processing method and a data processing apparatus for processing data collected by a mass spectrometer capable of performing an $MS^n$ analysis (where n is an integer equal to or more than two).

BACKGROUND ART

A comprehensive analysis is one of the methods of an analysis using a mass analysis. In the comprehensive analysis, all the results obtained from mass analyses for a plurality of samples are compared. In an analysis of this kind, a multivariate analysis is generally used such as a discrimination analysis, a principal component analysis, a cluster analysis, or other analysis.

For example, Non-Patent Document 1 discloses a software program for performing a principal component analysis of mass spectrum data obtained from a mass analysis. Non-Patent Document 2, Patent Document 1, and other documents disclose examples in which mass spectrum data obtained for a plurality of samples are processed by a principal component analysis and the results are presented using the charts called the "scores plot" and "loadings plot." The scores plot presents the results of the principal component analysis in such a manner as to enable users to easily recognize the grouping of plural samples. The loadings plot provides information about which compounds (components) contribute to the grouping of those samples and to what extent.

Some of the recently developed mass spectrometers can obtain $MS^1$ spectrum data, which are a result of an $MS^1$ analysis, and also $MS^2$ spectrum data, which are a result of an $MS^2$ analysis in which an ion dissociation operation is performed (for example, refer to Non-Patent Document 3). In such a mass spectrometer, immediately after a normal mass analysis ($MS^1$ analysis) is performed, a peak or peaks appearing on the $MS^1$ spectrum obtained by the $MS^1$ analysis are selected under predetermined conditions (for example, a predetermined number of peaks are selected in descending order of their peak intensity). Then, the mass-to-charge ratios of the selected peaks are set as the precursor ions, and the precursor ions are selected and dissociated. A variety of product ions generated by the dissociation are mass analyzed to obtain $MS^2$ spectrum data. Such $MS^n$ spectrum data generally include structural information on a target component, which is useful for the identification and structural analysis of the component.

Using $MS^n$ spectrum data in a comprehensive analysis probably allows a more accurate or more detailed analysis. However, the data used in the aforementioned conventional comprehensive analysis are mostly $MS^1$ spectrum data. Even in the case where an $MS^n$ analysis is performed, $MS^n$ spectrum data are merely used for the deduction of the composition of each component, database search, or other purposes after the comprehensive analysis using $MS^1$ spectrum data is completed.

BACKGROUND ART DOCUMENT

Patent Document

[Patent Document 1] JP-A 2009-25056

Non-Patent Document

[Non-Patent Document 1] "MarkerView™ Software", [online], Applied Biosystems, Internet, [Mar. 11, 2009]

[Non-Patent Document 2] Yonekubo and two other authors, "Saishin No Hikoujikan-gata Shitsuryobunseki-kei LCT Premier™ No Tokuchou To Shokuhin Metaborohmu Heno Ouyou (Feature of newest Time Of Flight Mass Spectrometer LCT Premier™ and Applied for Food Metabolome)," Chromatography, Vol. 27, No. 2(2006)

[Non-Patent Document 3] Iida and three other authors, "Application of LCMS-IT-TOF Mass Spectrometer for Proteomics Analysis," Shimadzu Review, vol. 63, Nos. 1 and 2, published on Sep. 29, 2006, pp. 19-28

DISCLOSURE OF THE INVENTION

Problem to be Solved by the Invention

The present invention has been developed to solve the aforementioned problem, and the objective thereof is to provide a mass analysis data processing method and a mass analysis data processing apparatus for effectively using, in a comprehensive analysis, all $MS^n$ spectrum data collected by an $MS^n$ analysis so as to obtain appropriate information for the identification and structural analysis of a variety of compounds.

Means for Solving the Problem

To solve the aforementioned problem, the first aspect of the present invention provides a mass analysis data processing method for processing data collected by a mass spectrometer capable of an $MS^n$ analysis (where n is an integer equal to or more than two), including:

a) an $MS^1$ data-analysis step for analysing $MS^1$ spectrum data collected by an $MS^1$ analysis;

b) an $MS^n$ data-analysis step for performing a multivariate analysis of a matrix in which $MS^n$ analysis information based on $MS^n$ spectrum data collected by an $MS^n$ analysis is described; and c) a display processing step for displaying, on a same window, a result of the data-analysis in the $MS^1$ data-analysis step and a result of the multivariate analysis in the $MS^n$ data-analysis step.

To solve the aforementioned problem, the second aspect of the present invention provides a mass analysis data processing apparatus for processing data collected by a mass spectrometer capable of an $MS^n$ analysis (where n is an integer equal to or more than two), including:

a) an $MS^1$ data-analyzer for analysing $MS^1$ spectrum data collected by an $MS^1$ analysis;

b) an $MS^n$ data-analyzer for performing a multivariate analysis of a matrix in which $MS^n$ analysis information based on $MS^n$ spectrum data collected by an $MS^n$ analysis is described; and c) a display processor for displaying, on a same window, a result of the data-analysis by the $MS^1$ data-analyzer and a result of the multivariate analysis by the $MS^n$ data-analyzer.

The $MS^n$ spectrum data collected by an $MS^n$ analysis include information such as the mass and the content of a portion of a compound contained in the sample. Such a portion may be the backbone structure of the compound or a fragment desorbed from the backbone structure by dissociation. Hence, for example, the result obtained by performing a multivariate analysis of a matrix in which $MS^n$ analysis information based on the $MS^n$ spectrum data is described reflects the information that the backbone structures of different compounds are similar or completely heterogeneous. The result obtained by analysing the $MS^1$ spectrum data collected by the $MS^1$ analysis reflects the relationships among a plurality of samples, the relationships among compounds obtained at different points in elution time (in the case of a chromatograph mass spectrometer), and other information. Therefore, for example, when a plurality of samples are analyzed, the display performed in the display processing step can show information for identifying samples which can be regarded as belonging to the same group, and also information on the similarity of the structure of the compounds characteristic of the group.

The result of the analysis in the $MS^1$ data-analysis step and the result of the multivariate analysis in the $MS^n$ data-analysis step may be overlapped on the same graph, e.g. a two-dimensional graph. This further clarifies the correspondence relationship between those two results.

In the first and second aspects of the present invention, for example, the matrix in which $MS^n$ analysis information is described may be a correlation coefficient matrix whose elements are correlation coefficients among $MS^n$ spectra corresponding to different precursor ions.

In order to create such a correlation coefficient matrix, in the mass analysis data processing method according to one embodiment of the first aspect of the present invention, the $MS^n$ data-analysis step may include:

a data set acquisition step for obtaining, for each of the precursor ions, a data set based on the collected $MS^n$ spectrum data, composed of peak intensity data at a mass-to-charge ratio of a product ion and/or a neutral loss, appearing on $MS^n$ spectra corresponding to the precursor ions; and a correlation coefficient matrix creation step for computing correlation coefficients between $MS^n$ spectra for different precursor ions by using the data sets corresponding to the precursor ions, and for creating a correlation coefficient matrix whose elements are the obtained correlation coefficients.

Similarly, in the mass analysis data processing apparatus according to the second aspect of the present invention, the $MS^n$ data-analyzer may include a data set acquirer for performing the data set acquisition step and a correlation coefficient matrix creator for performing the correlation coefficient matrix creation step.

In the mass analysis data processing method and apparatus of the aforementioned embodiment, a data set composed of peak intensity data at a mass-to-charge ratio of a product ion and/or a neutral loss appearing on $MS^n$ spectra corresponding to the precursor ions is obtained for each of the precursor ions. It is naturally possible that a peak originating from a product ion which appears on a $MS^n$ spectrum corresponding to one precursor ion does not exist on another $MS^n$ spectrum corresponding to a different precursor ion. In such a case, in the data set corresponding to the latter precursor ion, the peak intensity data at the mass-to-charge ratio of the nonexistent peak is set to be zero. Therefore, any of the data sets corresponding to the product ions contains the same number of data.

The data sets obtained in the aforementioned manner are used to calculate the correlation coefficient between $MS^n$ spectra for every possible combination of two precursor ions among a plurality of precursor ions and create a correlation coefficient matrix. If the number of the precursor ions is P, the correlation coefficient matrix is a P-by-P matrix. In the correlation coefficient matrix, the diagonal elements are all "1" and the upper and lower elements across the diagonal elements are symmetrical. By performing a multivariate analysis of such a correlation coefficient matrix, information on the mutual relationships of the $MS^n$ spectra can be obtained.

In the mass analysis data processing method according to the first aspect of the present invention and the mass analysis data processing apparatus according to the second aspect of the present invention, a network analysis can be used, for example, as a method of the multivariate analysis. In particular, in the $MS^n$ data-analysis step, a network analysis may be performed for an adjacency matrix created by replacing the diagonal elements of the correlation coefficient matrix by zeros, and information (e.g. a network map) visually showing mutual relationships among the precursor ions may be created.

The network analysis, which is based on the graph theory, has been generally used in the fields of communication network and sociology. In recent years, it has also been used in biological fields, such as the gene analysis (refer to JP-A 2006-323846 and other documents). The use of the network analysis makes possible a comprehensive and visual presentation of the similarity or difference among $MS^n$ spectra for different precursor ions obtained in an $MS^n$ analysis. In a network map, for example, one precursor ion (i.e. one $MS^n$ spectrum) is indicated with one data point, and data points correlating with each other are connected by directed or undirected lines. Plotting all the precursor ions on a network map enables analysis operators to recognize at a glance the mutual relationships among all the $MS^n$ spectra obtained by an analysis of one sample.

The creation of a network map from a correlation coefficient matrix or an adjacency matrix can be easily performed by using existing software.

In the mass analysis data processing method according to the first aspect of the present invention and the mass analysis data processing apparatus according to the second aspect of the present invention, any one method selected from a principal component analysis, a discrimination analysis, a cluster analysis, and a self-organizing map (SOM) analysis may be used as the method for the multivariate analysis.

The mass analysis data processing method as one embodiment of the first aspect of the present invention and the mass analysis data processing apparatus as one embodiment of the second aspect of the present invention:

data collected by a chromatograph mass spectrometer, such as a liquid chromatograph mass spectrometer or a gas chromatograph mass spectrometer, in which a mass spectrometer capable of an $MS^n$ analysis is used as a detector may be processed; and information visually showing mutual relationships among all precursor ions each having a different mass-to-charge ratio and retention time may be created.

In this embodiment, the mutual relationships among $MS^n$ spectra obtained at different retention times are also displayed on the network map. For example, if compounds having similar chemical structures are eluted at different retention times, their structurally similar portions are highly correlated. On the network map, two precursor ions ($MS^n$ spectra) corresponding to the structurally similar portions are displayed in such a manner that they are clearly related. Hence, looking at this network map, an analysis operator can intuitively comprehend that they have similar structures.

In the mass analysis data processing method according to the first aspect of the present invention and the mass analysis data processing apparatus according to the second aspect of the present invention, a variety of methods can be used for analysing the $MS^1$ spectrum data. For example, a multivariate analysis can be used, such as a principal component analysis, a partial least squares analysis (PLS), a PLS discriminant analysis (PLS-DA), or a cluster analysis. Alternatively, an analysis using a neural network may be used, such as a self-organizing map (SOM) analysis.

Performing a complicated computation processing such as a multivariate analysis is not always necessary; the result of the $MS^1$ analysis may be simply plotted on a two-dimensional graph having the retention time and the mass-to-charge ratio on the two axes. Or, the result of the $MS^1$ analysis may be plotted on a two-dimensional graph with a plurality of samples serially located on one axis and their mass-to-charge ratios on the other axis. Alternatively, the result of the $MS^1$ analysis may be plotted on a three-dimensional graph having three axes corresponding to a plurality of samples, the retention time, and the mass-to-charge ratio, respectively.

In the mass analysis data processing method as one embodiment of the first aspect of the present invention and the mass analysis data processing apparatus as one embodiment of the second aspect of the present invention, when any of the directed or undirected lines connecting data points is selected on the network map displayed on a window of a display unit, a product ion and/or a neutral loss which is common to the $MS^n$ spectra corresponding to the data points at both ends of the selected line may be displayed or expressly shown.

With this configuration, the product ions or neutral losses originating from the precursor ion in which the analysis operator is interested can be immediately located. This eliminates the cumbersome operation of displaying every $MS^n$ spectrum for the precursor ion of interest to check for the common product ions, which enhances the efficiency of the analysis operation of the sample.

On the network map, physical values corresponding to data points, such as a retention time, sample name, and/or mass-to-charge ratio of the precursor ion, may be displayed always or in response to an instruction.

When a plurality of data points are selected on the network map displayed on a window of the display unit, a peak or peaks (product ions or neutral losses) which are common to the $MS^n$ spectra corresponding to those data points may be displayed as a spectrum or in tabular form. Alternatively, when a plurality of data points are selected on the network map displayed on a window of the display unit, a peak or peaks (product ions or neutral losses) which are not common to the $MS^n$ spectra corresponding to those data points may be displayed as a spectrum or in tabular form.

The mass analysis data processing method as one embodiment of the first aspect of the present invention and the mass analysis data processing apparatus as one embodiment of the second aspect of the present invention may further include an identification process step or an identification processor for performing a database search for the $MS^1$ spectrum data (the information on the precursor ion such as the mass-to-charge ratio and retention time) and/or the $MS^n$ spectrum data to determine a compound name or chemical structure formula corresponding to a precursor ion, and the compound name or chemical structure formula determined in the identification process step or by the identification processor may be displayed on the network map displayed on a window of a display unit.

With this configuration, the network map showing the correlativity among the precursor ions and the result of identifying the compounds by a database search can be checked at the same time. Consequently, the analysis operator can have a better understanding of the plurality of compounds contained in the sample, and also easily compare a plurality of samples.

As previously described, the network analysis is an effective method for comprehensively and visually showing the mutual relationships among a plurality of precursor ions (or $MS^n$ spectra). Hence, in some cases, providing the analysis operator with only such information may be enough. In such cases, it is not necessary to show the result of the $MS^1$ data-analysis with the result of the $MS^n$ data-analysis.

That is, such a mass analysis data processing method for processing data collected by a mass spectrometer capable of an $MS^n$ analysis (where n is an integer equal to or more than two) may include a network analysis step for performing a network analysis of a matrix in which $MS^n$ analysis information based on $MS^n$ spectrum data collected by an $MS^n$ analysis is described, and for obtaining information showing the mutual relationships among precursor ions. More preferably, the mass analysis data processing method may further include a display processing step for displaying, on a window of a display unit, information visually showing the mutual relationships among precursor ions obtained by the network analysis.

Effects of the Invention

With the mass analysis data processing method according to the first aspect of the present invention and the mass analysis data processing apparatus according to the second aspect of the present invention, an analysis operator can easily comprehend the similarity or difference among the $MS^n$ analysis results for different precursor ions. Therefore, for example, it is possible to efficiently perform an analysis or evaluation of a sample containing a plurality of compounds. In addition, by comparing network maps created for each sample, the similarity or difference of different samples can be easily evaluated.

BRIEF DESCRIPTION OF THE DRAWINGS

FIG. 3 is a flowchart showing a procedure of a characterizing data processing in the LC/MS analysis system of the present embodiment.

FIG. 4 shows a format of an $MS^2$ spectrum data matrix.

FIG. 5 shows a format of a correlation coefficient matrix of $MS^2$ spectra.

FIG. 6 shows a format of an adjacency matrix of $MS^2$ spectra.

FIG. 7 shows a concrete example of the $MS^2$ spectrum data matrix.

FIG. 8 shows a concrete example of the correlation coefficient matrix of $MS^2$ spectra.

FIG. 9 shows a concrete example of an adjacency matrix of $MS^2$ spectra.

BEST MODE FOR CARRYING OUT THE INVENTION

Figure 1:
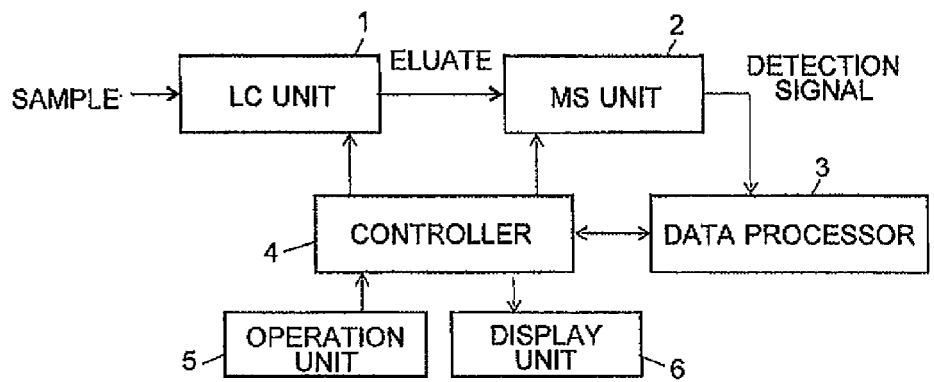
FIG. 1 is a schematic block configuration diagram of an embodiment of an LC/MS analysis system having a mass analysis data processing apparatus according to the present invention.
Figure 2A:
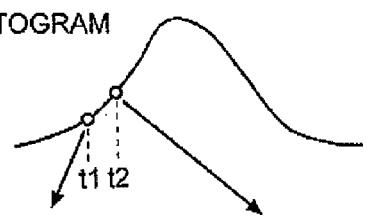
FIGS. 2A to 2C are an explanation diagram of a collection operation of $MS^n$ spectrum data in the LC/MS analysis system of the present embodiment.
Figure 2B:
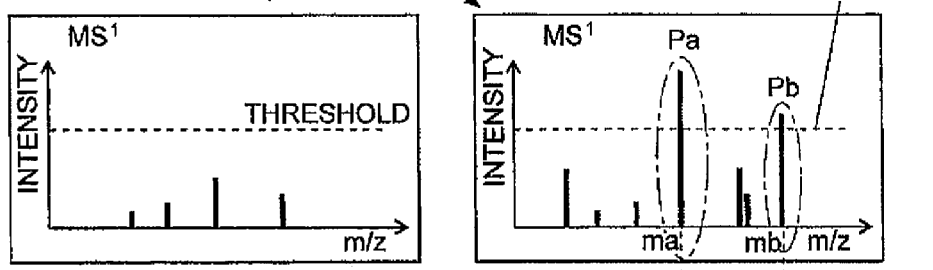
Figure 2C:
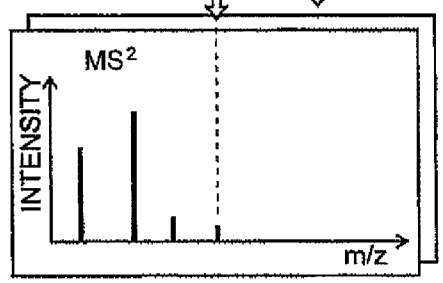

An embodiment of the mass analysis data processing method according to the present invention and the mass analysis data processing apparatus for performing this method will be described. As an example, an LC/MS analysis system having the mass analysis data processing apparatus is considered. FIG. 1 is a schematic block configuration diagram of this LC/MS analysis system, and FIGS. 2A to 2C are an explanation diagram of a collection operation of MS$^n$ spectrum data in this LC/MS analysis system.

As shown in FIG. 1, a sample to be analyzed is introduced into a liquid chromatograph (LC) unit 1. While passing through a column (not shown) included in the LC unit 1, a variety of components in the sample are temporally separated and sequentially exit. This eluate is introduced into a mass spectrometer (MS) unit 2.

Although not shown, the MS unit 2 may be, for example, an ion trap time-of-flight mass spectrometer (IT-TOFMS) including: an atmospheric pressure ion source (such as an electrospray ion source); an ion trap; a time-of-flight mass spectrometer, and an ion detector. In the MS unit 2, the sample components in the eluate introduced from the LC unit 1 are ionized and the generated ions are temporarily stored in the ion trap. A certain amount of kinetic energy is given to the stored ions in the ion trap and they are sent to the time-of-flight mass spectrometer. While flying in the flight space, the ions are separated in accordance with their mass-to-charge ratio and sequentially detected by the ion detector.

The detection signal obtained in the MS unit 2 is provided to a data processing unit 3, where the signal is converted into digital data and processed. The data processing unit 3 converts the time of flight of each ion obtained from the detection data into the mass-to-charge ratio, and creates a mass spectrum with the mass-to-charge ratio assigned to the horizontal axis and the signal intensity to the vertical axis. Further, as time progresses, the data processing unit 3 creates a total ion chromatogram and a mass chromatogram. In addition, the data processing unit 3 processes the obtained mass spectrum data in a characteristic way as will be described later.

The controller 4 controls the operations of the LC unit 1, the MS unit 2, and the data processing unit 3. Simultaneously, the controller 4 receives operations by an analysis operator through an operation unit 5 and a display unit 6 as a user interface, and provides an analysis result such as a mass spectrum. Most of the functions of the controller 4 and the data processing unit 3 can be realized by a personal computer in which a predetermined control/process software program is installed.

In the MS unit 2, the ion trap has the function of dissociating ions stored inside by a collision induced dissociation to generate product ions. When an MS² (=MS/MS) analysis is performed in the MS unit 2, a variety of ions are first stored in the ion trap. Then, the ion trap is driven so that only ions having a specific mass-to-charge ratio among the stored ions are selectively retained as precursor ions. Then, a collision-induced dissociation gas such as argon is introduced into the ion trap to accelerate the dissociation of the selected precursor ions. A variety of product ions generated by the dissociation are stored in the ion trap. Then, an energy is given to the product ions so that they are collectively ejected from the ion trap. They are introduced into the time-of-flight mass spectrometer and mass analyzed. Based on the thereby obtained detection signal, the data processing unit 3 obtains a mass spectrum of the product ions, i.e. the MS² spectrum.

In addition, an MS$^n$ analysis where n is equal to or more than three can be performed by selecting ions having a specific mass-to-charge ratio as a precursor ion among a variety of product ions generated by a dissociation and then performing a dissociation operation once again, or by repeating such selection and dissociation of ions. Theoretically speaking, the number of repetition of the dissociation operation is not limited. However, in many cases, the maximum value of n is practically in the range of approximately 3 through 6.

Next, a data collection operation using an automatic MS$^n$ function in this LC/MS analysis system will be described with reference to FIGS. 2A to 2C. After a sample is introduced into the LC unit 1, a general mass analysis is repeated at predetermined time intervals in the MS unit 2. Consequently, in the data processing unit 3, one mass spectrum (MS¹ spectrum) is created for each predetermined time intervals (refer to FIGS. 2A and 2B).

After one MS¹ spectrum is obtained, the data processing unit 3 immediately detects peaks appearing on the MS¹ spectrum, identifies a peak or peaks complying with predetermined conditions, and performs an MS² analysis in which an ion corresponding to one of the identified peaks is used as the precursor ion. For example, in FIGS. 2A to 2C, for the peaks appearing on the MS¹ spectrum, a predetermined number of peaks are selected in the descending order of their intensity among the peaks having a peak intensity equal to or higher than a threshold. As shown in FIG. 2B, in the MS¹ spectrum obtained at time t1, no peak complies with the aforementioned conditions. Therefore, no MS² analysis is performed. On the other hand, in the MS¹ spectrum obtained at time t2, two peaks comply with the conditions. Therefore, MS² analyses are immediately performed for P1 and then P2 in which mass-to-charge ratios ma and mb are respectively set as a precursor ion. Consequently, two MS² spectra are obtained: an MS² spectrum for the precursor ion having a mass-to-charge ratio of ma and an MS² spectrum for the precursor ion having a mass-to-charge ratio of mb.

The data collection by the automatic MS$^n$ function as just described is repeated from the point in time when the sample is introduced into the LC unit 1 until a predetermined period of time passes (generally, until all the sample components in a sample are eluted out). As a consequence, MS¹ spectra are obtained at predetermined time intervals, while one MS² spectrum is also obtained at each point in time when a peak complying with predetermined conditions is found. The data composing such mass spectra, i.e. MS¹ spectrum data and MS$^n$ spectrum data, are stored in a memory unit of the data processing unit 3.

For the data collected in the aforementioned manner, the data processing unit 3 performs a characterizing data processing as will be described. FIG. 3 is a flowchart showing a processing procedure of this characterizing data processing.

First, all MS² spectrum data are collected from the data collected for one sample (Step S1). MS² spectrum data compose an MS² spectrum obtained for a precursor ion having a certain mass-to-charge ratio at a certain retention time (elution, time), and include data which indicate the mass-to-charge ratio and the intensity value of each peak appearing on the MS² spectrum. In this embodiment, precursor ions each having a different retention time RT and a mass-to-charge ratio M are described as $P_n$ (n=1 through x).

Subsequently, a data matrix as shown in FIG. 4 is created from the collected MS² spectrum data (Step S2). In this data matrix, the precursor ions $P_n$ are arrayed in the horizontal direction and the mass-to-charge ratios of the product ions $m_m$ (m=1 through y) (or the mass-to-charge ratio of a neutral loss; i.e. the difference between the mass-to-charge ratio of a precursor ion and that of a product ion) in the vertical direction. In this embodiment, the peak intensity of a product ion having mass-to-charge ratio $m_m$ on an MS² spectrum corresponding to a precursor ion $P_n$ is denoted by $I_{nm}$. For example, in the MS² spectrum corresponding to the precursor ion $P_0$, the peak intensity of a product ion whose mass-to-charge ratio is $m_2$ is $I_{02}$. The shown list of the mass-to-charge ratios $m_m$ of the product ions includes the mass-to-charge ratios of all the product ions appearing on the MS² spectra corresponding to all the precursor ions. Hence, in an MS² spectrum corresponding to a certain precursor ion, there are many mass-to-charge ratios $m_m$ at which there is no peak. When there is no peak at a certain mass-to-charge ratio as just described, the intensity $I_{nm}$ for this mass-to-charge ratio $m_m$ is set at zero. In this embodiment, y pieces of data ($I_{n1}$, $I_{n2}$, $I_{n3}$, $I_{n4}$, ..., and $I_{ny}$) corresponding to one precursor ion $P_n$ (or forming one MS² spectrum) are called a "data set." In FIG. 4, y pieces of peak intensity data contained in one column compose one data set.

For the sake of easy understanding, an example of concrete values is shown in FIG. 7. This is a part of the MS² spectrum data matrix shown in FIG. 4. For example, FIG. 7 shows that, in the MS² spectrum corresponding to the precursor ion $P_0$ with a retention time RT of 14.24333 and a mass-to-charge ratio M of 455.2913, a peak with an intensity of 0.0574 exists at a mass-to-charge ratio of 103.7293. It also shows that, in the MS² spectrum corresponding to this precursor ion $P_0$, there is no peak at the mass-to-charge ratio of 106.0751, at which a peak exists in an MS² spectrum corresponding to another precursor ion $P_3$.

Next, for every possible combination of two data sets selected from a total of x precursor ions, i.e. a total of x MS² spectra, the correlation coefficient R is computed by a known computational method. After the correlation coefficients R are obtained for all the combinations, an x-by-x correlation coefficient matrix whose elements are the correlation coefficients R is created, as shown in FIG. 5 (Step S3). For example, the correlation coefficient between the MS² spectrum corresponding to the precursor ion $P_1$ and the MS² spectrum corresponding to the precursor ion $P_2$ is $R_{1,2}$. In the correlation coefficient matrix, all the diagonal elements are "1" because they are correlated with themselves. In addition, with respect to these diagonal elements, the upper and lower matrix elements are symmetrical. FIG. 8 shows a correlation coefficient matrix obtained from an MS² spectrum data matrix which is partially shown in FIG. 7.

Next, the information of the correlation coefficient matrix obtained in the aforementioned manner is shown by a graph to aid an easy understanding. To this end, as shown in FIG. 6, all the "1s" of the diagonal elements of the correlation coefficient matrix are replaced by "0s" and this matrix is defined as an adjacency matrix for the network analysis (Step S4). FIG. 9 shows the adjacency matrix obtained from the correlation coefficient matrix shown in FIG. 7. A network analysis is performed for the adjacency matrix obtained in this manner to create a network map (Step S5).

The network analysis is based on the so-called graph theory. In order to create a network map from an adjacency matrix, any of the existing software products that can be easily obtained (e.g. a software package named "igraph") may be used. In a network map, the relationship between data points is shown by lines. The graph is either a directed graph in which the lines are directed, or an undirected graph in which the lines are undirected. In this embodiment, the network map is an undirected graph, since each data point represents one precursor ion or one MS² spectrum and the correlation between any two data points is undirected. (This is why the correlation coefficient matrix is vertically symmetrical with respect to the diagonal elements.).

Figure 10:
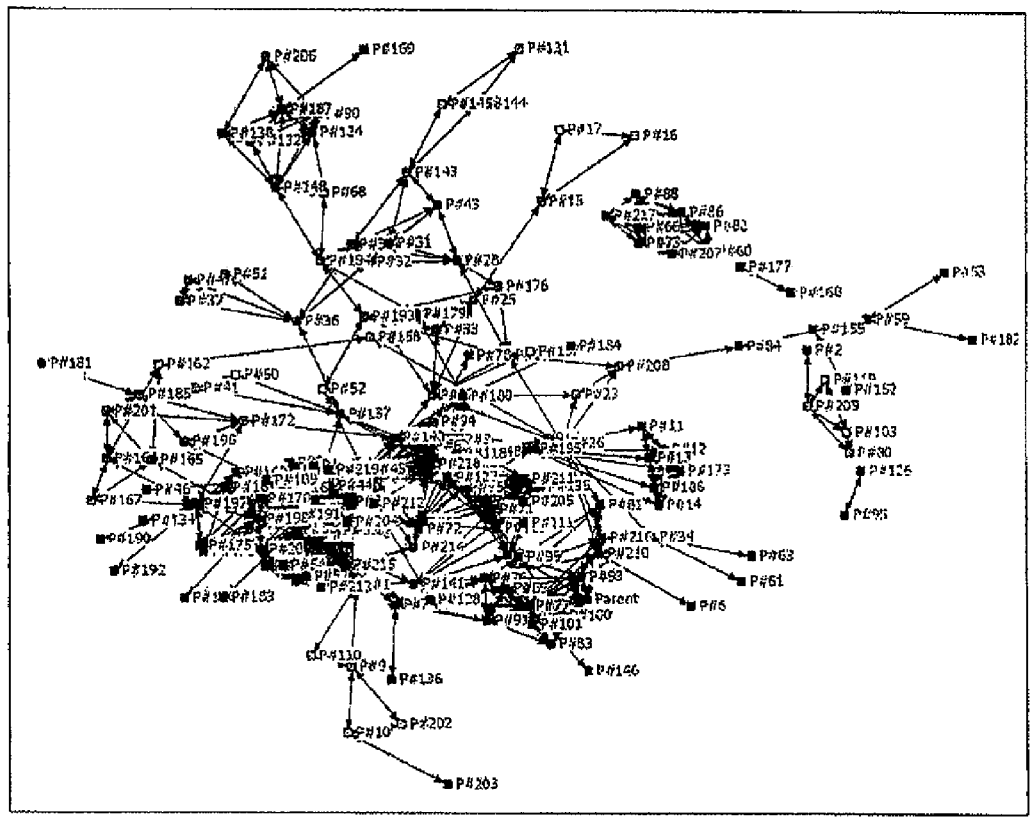
FIG. 10 shows a concrete example of a network map of MS² spectra.

The network map allows various changes in terms of the arrangement of data points and the display of lines. For example, the data points may be shown in mutually different colors, with highly-correlated data points being arranged as close to each other as possible. FIG. 10 shows an example of the network map created from the example shown in FIGS. 7 through 9. In this example, the shorter a line is, the higher the correlation is. If there is no correlation, there is no line. However, a threshold may be set for the correlation coefficient, and any data points having a correlation coefficient equal to or lower than the threshold may be considered to be uncorrelated. A network map as shown in FIG. 10 visualizes the correlations among different MS² spectra, facilitating the understanding thereof.

Figure 12:
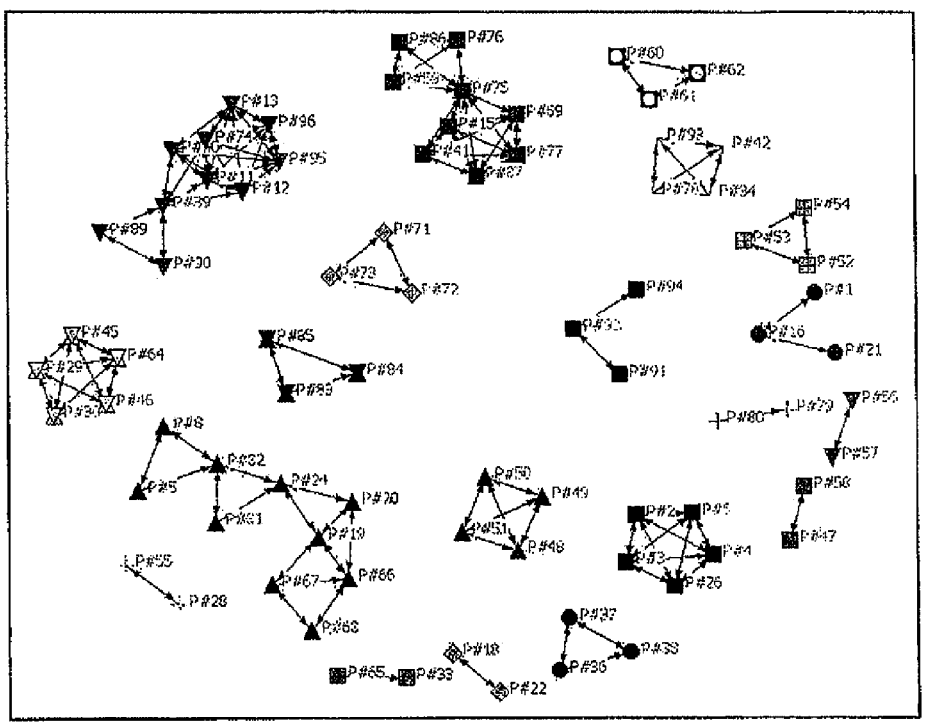
FIG. 12 shows another concrete example of a network map of MS² spectra.

In the example of FIG. 10, the data points are connected with undirected lines so as to show that these data points belong to a certain group having a correlation. There are other possible modifications, such as using the same display color for the correlated data points belonging to the same group or uniforming the shape of the data points belonging to the same group. FIG. 12 is an example of a network map in which the color and shape of the data points belonging to a group having a correlation are the same and the data points are connected with undirected lines.

However, the network map of MS² spectrum as previously described does not reflect information on any peaks which did not comply with predetermined criteria in the MS¹ analysis result. Given this factor, the controller 4 creates display data in which the analysis result obtained by analyzing the MS¹ analysis result (MS¹ spectrum data) and the network map of the MS² spectra are placed in the same window. Then, the controller 4 provides the display data to the display unit 6 to display them in a display window (Step S6). There are a variety of possible methods for analyzing MS¹ spectrum data.

Figure 11:
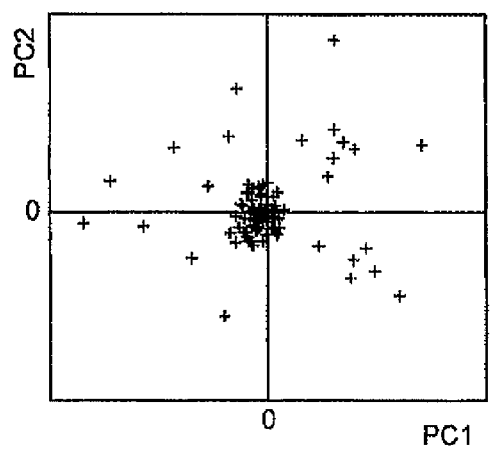
FIG. 11 shows an example of an analysis result of an MS¹ spectrum data.

For example, as described in Patent Document 1, a principal component analysis, which is a kind of multivariate analysis, is applied to MS¹ spectrum data having the three dimensions of a retention time, mass-to-charge ratio, and a signal intensity, so as to compute the loading corresponding to each compound contained in a sample. Then, a loadings plot is created in which the computed loading values are plotted on a graph having two orthogonal axes representing two principal components (for example, refer to FIG. 11). The loadings plot may be displayed as a result of the MS¹ spectrum data on a window of the display unit 6.

Other than the principal component analysis, the multivariate analysis method may be the partial least squares (PLS) method, PLS discriminant analysis (PLS-DA) method, cluster analysis, or other method. Another possible choice is a self-organizing map (SOM) analysis, which is a kind of the neural network. It is also possible to omit such a complicated computation processing and merely plot the data obtained by an MS¹ analysis on a two-dimensional graph having two orthogonal axes representing the retention time and the mass-to-charge ratio.

Figure 13A:
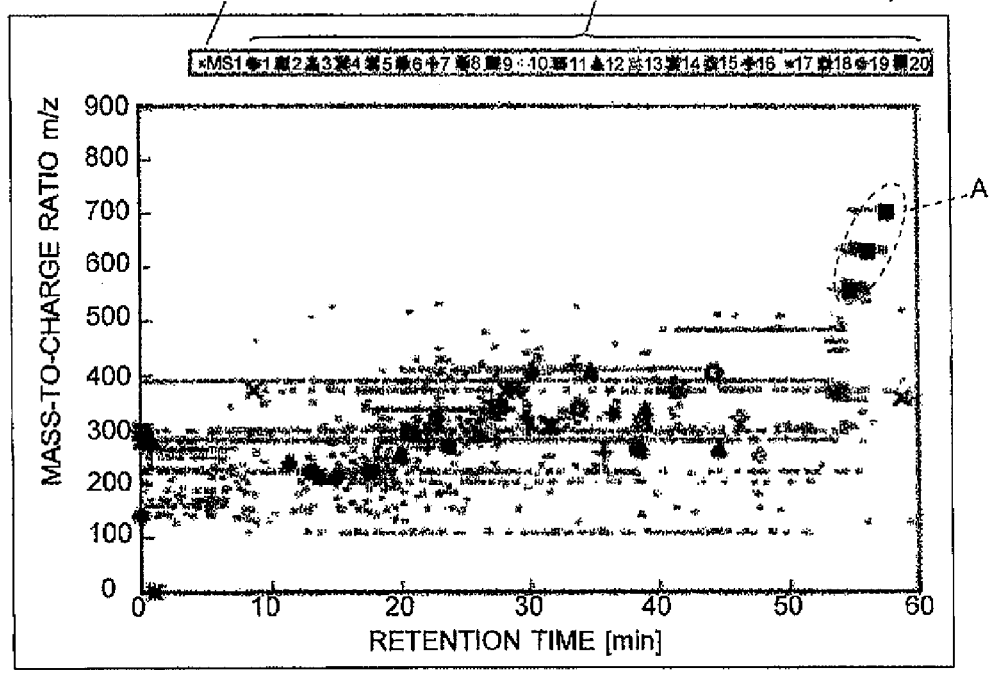
FIGS. 13A and 13B show an example of an overlapping display of the result of an MS¹ data-analysis and the result of an MS² multivariate analysis.
Figure 13B:
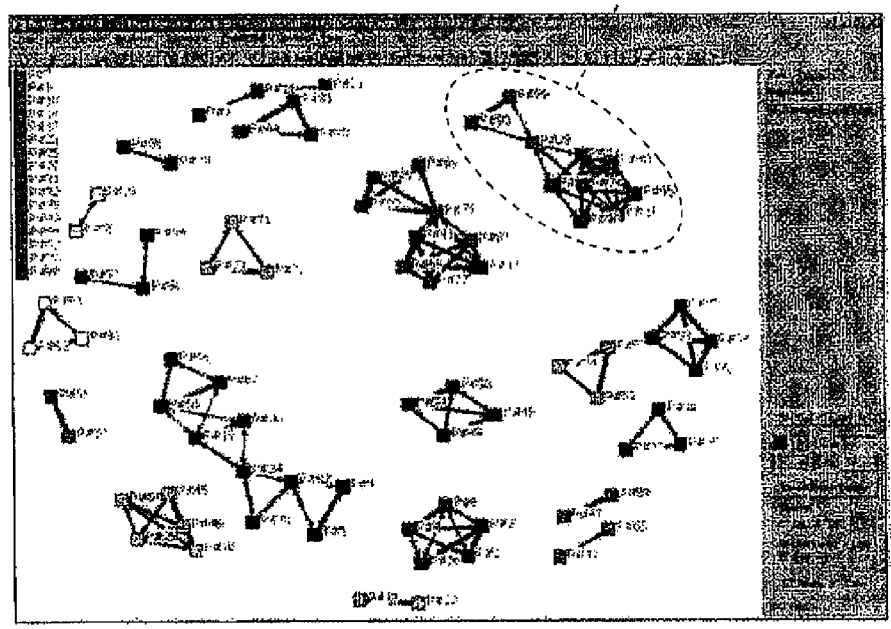

In Step S6, the display data in which the result of an $MS^1$ analysis and the result of $MS^2$ multivariate analyses (network map) are presented in the same window is provided to the display unit 6. However, both the results may be plotted on the same graph to further clarify their correspondence relationship. FIGS. 13A and 13B show an example of such an overlapping of the two results. FIG. 13A shows a two-dimensional graph having two orthogonal axes representing the retention time and the mass-to-charge ratio, on which various points are plotted, where the points indicated by small dots each correspond to one peak on the mass spectrum obtained by an $MS^1$ analysis, while the points indicated by various symbols, such as ●, ○ or ▲ correspond to the precursor ions and have different shapes and colors so that clusters which were each determined to have a correlation by a network analysis of the $MS^2$ spectrum data can be discriminated from each other. FIG. 13B shows a network map for this case. On this network map, a plurality of precursor ions mutually connected with lines form one cluster as surrounded by the dashed line. In this example, there are 20 clusters, which vary in the number of precursor ions forming one cluster.

An image in which the result of an $MS^1$ analysis and the result of an $MS^2$ multivariate analysis are superimposed on each other as shown in FIG. 13A on a window of the display unit 6 clearly illustrates the distribution of the mass-to-charge ratio and retention time of a plurality of precursor ions belonging to the same cluster. For example, an analysis operator can notice at a glance that the precursor ions in the area A surrounded by the dashed line in FIG. 13A belong to the same cluster and are located at approximately constant intervals of retention time with their mass-to-charge ratios almost constantly increasing. Such information cannot be easily found by only looking at the network map shown in FIG. 13B. By contrast, the information displayed as shown in FIG. 13A is easily understandable and useful for deducing the kind and structure of the compounds contained in a sample.

In the example of a network map shown in FIG. 10, each data point is labeled with only a sequence number ($P_n$) assigned to the precursor ion. Preferably, more detailed and useful information may be displayed in response to a predetermined operation on this network map by an analysis operator. For example, in response to the selection of a line connecting two data points with a pointing device such as a mouse included in the operation unit 5, the product ion or neutral loss which is common to the $MS^2$ spectra of the data points at two ends of the selected line may be displayed on the network map. In addition, when a known database search is performed for $MS^2$ spectrum data to identify compounds, the name or structure (such as the structural formula) of the identified compound may be displayed at an appropriate location, e.g. in the vicinity of the corresponding data point on the network map.

When a plurality of samples are compared, a network map of $MS^2$ spectra may be created for each sample in the same manner, and the position of data points, the degree of their aggregation, the connection state of the lines on the network map may be compared. This facilitates the understanding of the similarity or difference of the samples.

In the aforementioned embodiment, a network map is created by using $MS^2$ spectrum data. However, it is evident that a network map for $MS^n$ spectrum data, such as $MS^3$ or $MS^4$ spectrum data, can be created in the same manner. In this case, for example, if the precursor ions used in a plurality of $MS^n$ analyses with different values of n have the same mass-to-charge ratio, the product ions appearing on the $MS^n$ spectra respectively obtained for these precursor ions may be integrated to be treated as product ions corresponding to one precursor ion.

It is evident that the present invention can be applied to not only an LC/MS as in the aforementioned embodiment but also to a GC/MS. The present invention is even applicable to a mass spectrometer without a chromatograph. However, when the number of compounds contained in a sample is one or a few and the number of peaks appearing on an $MS^1$ spectrum is small, there is no advantage of using the present invention.

It should be noted that the embodiment described thus far is merely an example of the present invention, and it is evident that any modification, adjustment, or addition appropriately made within the spirit of the present invention is also included in the scope of the claims of the present application.

EXPLANATION OF NUMERALS

1 . . . LC Unit (Liquid Chromatograph Unit)
2 . . . MS Unit (Mass Spectrometer Unit)
3 . . . Data Processor
4 . . . Controller
5 . . . Operation Unit
6 . . . Display Unit

What is claimed is:

1. A mass analysis data processing method for processing data collected by a mass spectrometer capable of an $MS^n$ analysis where n is an integer equal to or more than two, comprising:
   providing a mass spectrometer unit with samples for analysis;
   running the mass spectrometer unit to collect $MS^1$ and $MS^n$ spectrum data based on the samples provided;
   executing an $MS^1$ data-analysis step for analyzing the $MS^1$ spectrum data collected by the mass spectrometer unit;
   executing an $MS^n$ data-analysis step for performing a multivariate analysis of a matrix in which $MS^n$ analysis information based on the $MS^n$ spectrum data collected by the mass spectrometer unit is described; and
   executing a display processing step for displaying, on a same window, a result of the analysis processing in the $MS^1$ data-analysis step and a result of the multivariate analysis in the $MS^n$ data-analysis step.

2. The mass analysis data processing method according to claim 1, wherein:
   the multivariate analysis is any one method selected from a principal component analysis, a discrimination analysis, a cluster analysis, and a self-organizing map (SOM) analysis.

3. The mass analysis data processing method according to claim 1, further comprising:
   processing the data collected by a chromatograph mass spectrometer in which the mass spectrometer unit capable of an $MS^n$ analysis is used as a detector; and
   creating information visually showing mutual relationships among all precursor ions each having a different mass-to- charge ratio and retention time.

4. The mass analysis data processing method according to claim 1, wherein:
   a multivariate analysis is performed in the $MS^1$ data-analysis step.

5. The mass analysis data processing method according to claim 4, wherein:
   an analysis by a neural network is performed in the $MS^1$ data-analysis step.

6. The mass analysis data processing method according to claim 4, wherein:
in the $MS^1$ data-analysis step, a result of the $MS^1$ analysis is plotted on a two-dimensional graph having a retention time and a mass-to-charge ratio on two axes.

7. The mass analysis data processing method according to claim 4, wherein:
in the $MS^1$ data-analysis step, a result of the $MS^1$ analysis is plotted on a three-dimensional graph having three axes corresponding to a plurality of samples, a retention time, and a mass-to-charge ratio, respectively.

8. The mass analysis data processing method according to claim 1, wherein:
the matrix in which $MS^n$ analysis information is described is a correlation coefficient matrix whose elements are correlation coefficients among $MS^n$ spectra corresponding to different precursor ions.

9. The mass analysis data processing method according to claim 8, wherein:
the $MS^n$ data-analysis step includes:
a data set acquisition step for obtaining, for each of the precursor ions, a data set based on the collected $MS^n$ spectrum data, composed of peak intensity data at a mass-to-charge ratio of a product ion and/or a neutral loss appearing on $MS^n$ spectra corresponding to the precursor ions; and
a correlation coefficient matrix creation step for computing correlation coefficients between $MS^n$ spectra for different precursor ions by using the data sets corresponding to the precursor ions, and for creating a correlation coefficient matrix whose elements are the obtained correlation coefficients.

10. The mass analysis data processing method according to claim 9, wherein:
in the $MS^n$ data-analysis step, a network analysis is performed for an adjacency matrix created by replacing diagonal elements of the correlation coefficient matrix by zeros, and information visually showing mutual relationships among the precursor ions is created.

11. The mass analysis data processing method according to claim 2, wherein:
in the $MS^n$ data-analysis step, a network analysis is performed for an adjacency matrix created by replacing diagonal elements of the correlation coefficient matrix by zeros, and information visually showing mutual relationships among the precursor ions is created.

12. The mass analysis data processing method according to claim 11, wherein the information created by the network analysis a network map.

13. The mass analysis data processing method according to claim 1, wherein the multivariate analysis is a network analysis.

14. The mass analysis data processing method according to claim 13, wherein the information created by the network analysis a network map.

15. The mass analysis data processing method according to claim 14, wherein:
when any of directed or undirected lines connecting data points is selected on the network map displayed on a window of a display unit, a product ion and/or a neutral loss which is common to $MS^n$ spectra corresponding to data points at both ends of the selected line is displayed.

16. The mass analysis data processing method according to claim 14, further comprising:
an identification process step for performing a database search for the $MS^1$ spectrum data and/or the $MS^n$ spectrum data to determine a compound name or chemical structure formula corresponding to a precursor ion, wherein:
the compound name or chemical structure formula determined in the identification process step is displayed on the network map displayed on a window of a display unit.

17. The mass analysis data processing method according to claim 14, wherein:
one or more kinds of data selected from a retention time, sample name, and mass-to-charge ratio of a precursor ion, each corresponding to a data point, are displayed always or in response to an instruction.

18. A mass analysis data processing apparatus for processing data collected by a mass spectrometer capable of an $MS^n$ analysis where n is an integer equal to or more than two, comprising:
a mass spectrometer unit for collecting $MS^1$ and $MS^n$ spectrum data based on samples provided to the mass spectrometer unit;
an $MS^1$ data-analyzer for analyzing the $MS^n$ spectrum data collected by the mass spectrometer unit;
an $MS^n$ data-analyzer for performing a multivariate analysis of a matrix in which $MS^n$ analysis information based on the $MS^n$ spectrum data collected by the mass spectrometer unit is described; and
a display unit for displaying, on a same window, a result of the analysis by the $MS^1$ data-analyzer and a result of the multivariate analysis by the $MS^n$ data-analyzer.

19. A mass analysis data processing method for processing data collected by a mass spectrometer capable of an $MS^n$ analysis where n is an integer equal to or more than two comprising:
providing a mass spectrometer unit with samples;
running the mass spectrometer to collect $MS^n$ spectrum data based on the samples provided;
executing a network analysis step for performing a network analysis of a matrix in which $MS^n$ analysis information based on the $MS^n$ spectrum data collected by the mass spectrometer unit is described, and for obtaining information showing the mutual relationships among precursor ions; and
executing a display processing step for displaying, on a window of a display unit, information visually showing mutual relationships among precursor ions obtained by the network analysis.

* * * * *